United States Patent [19]

Banitt et al.

[11] 4,013,670

[45] Mar. 22, 1977

[54] DERIVATIVES OF PYRROLIDINE AND PIPERIDINE

[75] Inventors: Elden H. Banitt, Woodbury; William R. Bronn, St. Paul, both of Minn.

[73] Assignee: Riker Laboratories, Inc., Northridge, Calif.

[22] Filed: May 27, 1975

[21] Appl. No.: 580,890

Related U.S. Application Data

[62] Division of Ser. No. 457,099, April 1, 1974, Pat. No. 3,900,481.

[52] U.S. Cl. .............. 260/295 AM; 260/295.5 A; 260/326.47; 424/263
[51] Int. Cl.² ................................. C07D 213/26
[58] Field of Search ............ 260/295 AM, 295.5 A, 260/326.47

[56] References Cited

UNITED STATES PATENTS

| | | | |
|---|---|---|---|
| 3,270,026 | 8/1966 | Berger et al. | 260/295 AM |
| 3,509,166 | 4/1970 | Wright, Jr. et al. | 260/295 AM |
| 3,655,677 | 4/1972 | Anello et al. | 260/295 AM |
| 3,655,728 | 4/1972 | Mendel | 424/308 |
| 3,719,687 | 3/1973 | Mendel et al. | 260/326.3 |
| 3,923,820 | 12/1975 | Roldan et al. | 260/295 AM |

Primary Examiner—Norman A. Drezin
Attorney, Agent, or Firm—Cruzan Alexander; Donald M. Sell; Donald C. Gipple

[57] ABSTRACT

Certain compounds in which a carbon atom of a pyrrolidine or piperidine ring is bonded directly or through a methylene group to the nitrogen of a substituted benzamido group, and their pharmaceutically acceptable salts, are found to be active as antiarrhythmic agents.

8 Claims, No Drawings

DERIVATIVES OF PYRROLIDINE AND PIPERIDINE

BACKGROUND OF THE INVENTION

This is a division of application Ser. No. 457,099 filed Apr. 1, 1974, now U.S. Pat. No. 3,900,481.

This invention relates to certain compounds in which a carbon atom of a pyrrolidine or piperidine ring is bonded directly or through a methylene group to the nitrogen of a substituted benzamido group, and their pharmaceutically acceptable salts. The benzamido group of these compounds is substituted by one to three 1,1-dihydroperfluoroalkoxy substituents. The compounds and their pharmaceutically acceptable salts are active as antiarrhythmic agents. The invention also relates to certain novel intermediates and to processes useful to prepare the compounds.

Esters of benzoic acid substituted on the aromatic ring by 1,1-dihydroperfluoroalkoxy substituents are described in U.S. Pat. No. 3,655,728. Certain amides of benzoic acid substituted on the aromatic ring by 1,1-dihydroperfluoroalkoxy substituents are described in U.S. Pat. No. 3,719,687. The novel compounds of the present invention differ structurally from those disclosed in U.S. Pat. No. 3,719,687 in that 1. all of the compounds of the present invention are bonded to the benzamido nitrogen atom through a methylene group or carbon nitrogen bond to a carbon of the pyrrolidine or piperidine ring, 2. the compounds may be either secondary or tertiary amines and 3. in the present invention only one or no carbon atoms link the benzamido nitrogen atom to a pyrrolidine or piperidine ring. Also, preferably and in most cases the compounds of the invention have an asymmetric center (i.e. carbon atom). The compounds of the present invention have, in general, an improved therapeutic ratio over the compounds of the prior art.

DETAILED DESCRIPTION OF THE INVENTION

This invention relates to chemical compounds and their pharmaceutically acceptable salts, processes for using the compounds of the invention, pharmaceutical compositions containing the compounds, processes for the preparation of the compounds and novel intermediates useful in the processes of the invention.

The compounds of the invention are broadly described as follows:

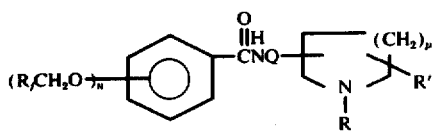

wherein $R_f$ is a perfluoroalkyl radical containing one to three carbon atoms ($C_mF_{2m+1}$ where $m$ is 1–3) $n$ is one to three, $p$ is one or two, Q is a carbon-nitrogen bond, methylene (—$CH_2$—), or methylmethylene (—$CH(CH_3)$—), and R and R' are hydrogen, methyl or ethyl.

Presently preferred are compounds of the invention wherein Q is 1) a carbon-nitrogen bond and is bonded to the 3 position of the pyrrolidine or piperidine ring or 2) a methylene or methylmethylene linking group and is bonded to the 2 position of the pyrrolidine or piperidine ring. These compounds are preferred because of generally greater anti-arrhythmic potency as detected by screening tests in animals. Some of them have also been found to have reduced side effects when compared to the compounds of the prior art, such as the compounds of Examples 15, 27 and 25. Other salts of these free bases also have reduced side effects.

Compounds of the invention wherein $n$ is two, $R_f$ is $CF_3$ and the orientation of the dihydroperfluoroethoxy groups is 2,5 are also presently preferred.

In the compounds of the invention which have at least one asymmetric carbon, the carbon atom of the pyrrolidine or piperidine ring to which the group Q is bonded, can be resolved to optically active enantiomers by methods known to the art. In addition, other asymmetric centers are possible, e.g. when Q is alkylmethylene or R' is methyl or ethyl. All of these optical isomers are included within the scope of the invention.

The compounds can be used directly or in the form of pharmaceutically acceptable acid-addition salts, especially as soluble acetic, hydrochloric, sulfuric or phosphoric acid salts. Other such salts include combinations with hydrobromic acid, sulfamic acid, methanesulfonic acid, benzenesulfonic acid, ethanedisulfonic acid, citric acid, maleic acid, oxalic acid, succinic acid, malic acid, fumaric acid, and tartaric acid. Pharmaceutically acceptable quaternary ammonium salts are also used, for example alkyl iodide and bromide salts.

The compounds of the invention are generally active as antiarrhythmics, although both the activity (exhibited by the test methods presently available) and the therapeutic indices vary from compound to compound. The antiarrhythmic activity of compounds is manifested in their ability to block chloroform-induced ventricular fibrillation in mice, as demonstrated by the test procedure described in detail by J. W. Lawson, J. Pharmacol. Exp. Therap. 160:22-31, 1968.

Presently preferred compounds of the invention having high antiarrhythmic activity are:

2,5-bis(2,2,2-trifluoroethoxy)-N-(3-piperidyl)benzamide 2,5-bis(2,2,2-trifluoroethoxy)-N-(2-piperidylmethyl)-benzamide 2,5-bis(2,2,2-trifluoroethoxy)-N-[(6-methyl-2-piperidyl)-methyl]benzamide 2,5-bis(2,2,2-trifluoroethoxy)-N-[1-(2-piperidyl)ethyl]-benzamide 2,5-bis(2,2,2-trifluoroethoxy-N-[(1-ethyl-2-piperidyl)-methyl]benzamide 2,5-bis(2,2,2-trifluoroethoxy)-N-[(1-ethyl-2-pyrrolidyl)-methyl]benzamide 2,5-bis(2,2,2-trifluoroethoxy)-N-[(1-methyl-2-piperidyl)-methyl]benzamide and pharmaceutically acceptable salts thereof.

In clinical practice, the derivatives of the invention will normally be administered as antiarrhythmics orally or by injection in the form of pharmaceutical preparations comprising the active ingredient in the form of the free base or one of the common therapeutically acceptable salts, e.g., the acetate or hydrochloride, in association with a pharmaceutically acceptable carrier. The carrier may be a solid, semi-solid or liquid diluent or an ingestible capsule. Usually the active substance will comprise between 0.01 percent and 5 percent of preparations intended for injection and between 10 percent and 80 percent of preparations intended for oral administration. Particularly preferred for intravenous use are 0.05–1.0 percent aqueous solutions of the active compounds buffered with sodium acetate to pH of about 5–7 and, for oral use, 20–60 percent formulations of the active ingredient in mannitol, lactose of potato starch.

Pharmaceutical preparations in the form of dosage units for oral administration containing a compound of the invention in the form of the free base or a pharmaceutically acceptable acid addition salt may be prepared in various ways. The compounds may be mixed with a solid, pulverulent carrier, for example lactose, saccharose, sorbitol, mannitol, starches such as potato starch, corn starch or amylopectin, cellulose derivatives, gelatin. The carrier may also be a lubricant such as magnesium or calcium stearate, a Carbowax or other polyethylene glycol wax compressed to form tablets or, preferably, cores which are then coated with a concentrated sugar solution which may contain, e.g., gum arabic, gelatin, talcum and/or titanium dioxide.

Soft gelatin capsules (pearl-shaped, closed capsules) and other closed capsules consist, for example, of a mixture of gelatin and glycerol, and contain, e.g., mixtures of the active substance with a vegetable oil, and hard gelatin capsules contain, for example, granulates of the active substance with solid, pulverulent carriers such as lactose, saccharose, sorbitol, mannitol; starches such as potato starch, corn starch or amylopectin; cellulose derivatives or gelatin, as well as magnesium stearate or stearic acid.

For parenteral application by injection the preparations of the invention advantageously comprise an aqueous, generally saline, solution of a water soluble, pharmaceutically acceptable salt of the active substance and optionally also a stabilizing agent and/or a buffer substance, e.g. sodium acetate.

In addition, some of the compounds of the present invention exhibit activity as local anesthetics. These compounds can be administered by topical application to produce surface anesthesia and used to relieve itching, burning and surface pain or by local injection for surgical procedures. When they are administered topically the compounds are generally administered from aqueous solutions, in pharmaceutical cream or salve bases, etc. When injected as anesthetics the compounds can be conveniently used as solutions, for example, in aqueous solutions which may be made isotonic, for example, by the addition of sodium chloride. The local anesthetic activity is observed using the corneal reflex test using rabbits as test animals. This test method is described by F. P. Luduena and J. O. Hoppe, J. Pharmacol. Ex. Therap., 104:40, 1952.

The compounds of the invention, other than those in which Q is a carbon-nitrogen bond connected to the 2 position of the heterocyclic ring, can be prepared by reacting a compound of the formula:

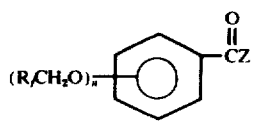

II wherein Z is halogen, preferably chlorine, or a 1,1-dihydroperfluoroalkoxy group containing one to four carbon atoms, and $R_f$ and $n$ are as defined hereinabove with an aminomethyl- or amino-pyrrolidine or piperidine of the formula:

III wherein Q, R, R' and p are as previously defined, except that when Q is in the 2 position it is not a carbon-nitrogen bond. The reaction is carried out in an inert solvent such as benzene, glyme, toluene or diethyl ether. Preferably R is not hydrogen. An acid acceptor such as a tertiary amine is usually used when Z is halogen. When Z is a 1,1-dihydroperfluoroalkoxy group, the reaction is generally carried out by refluxing the reactants without solvent or with an inert solvent such as glyme, followed by isolation of the product.

An alternative procedure which is generally useful, but particularly useful in the preparation of the compounds in which Q is a carbon-nitrogen bond in the 2 position, comprises reacting an amino- or aminomethylpyrrole or pyridine with a compound of Formula II and selectively reducing the resulting substituted pyridine or pyrrole derivative (IV) as follows:

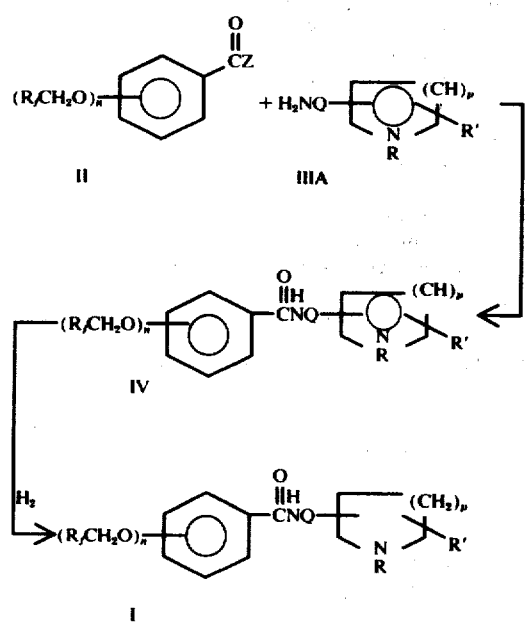

wherein $R_f$, $n$, Z, Q, $p$, R and R' are as previously defined, (Z being either halogen or 1,1-dihydroperfluoroalkoxy and Q being a carbon-nitrogen bond, methylene or methylmethylene), provided, however, that where the second reactant is a substituted pyridine (i.e., $p$ is 2), R in that compound and in the intermediate compound IV is not present (the valences of the nitrogen atom all being satisfied in the conjugated ring). This process, and the intermediate substituted pyridines and pyrroles (IV), are novel and form further aspects of the invention.

The intermediates (IV) are prepared using reaction conditions similar to those used in the previously described one-step process, depending upon whether Z is halogen or 1,1-dihydroperfluoroalkoxy. They are then reduced selectively using catalytic reduction to the corresponding piperidine and pyrrolidine derivatives of Formula I. The presently preferred catalyst for the catalytic reduction is platinum oxide. The reduction is generally run under acidic conditions, for example in acetic acid as solvent in the presence of hydrogen chloride.

The compounds of Formula II can be conveniently prepared from the corresponding acids (that is, compounds of Formula II where Z is OH), said acids being known to the art. See, for example U.S. Pat. No. 3,655,728. The compounds in which Z is halogen, e.g. chlorine, can be prepared by refluxing the acids with an excess of thionyl halide (chloride) in the presence of a small amount of dimethyl formamide. The excess thionyl halide is then removed by distillation. The compounds of Formula II in which Z is 1,1-dihydroperfluoroalkoxy are disclosed in U.S. Pat. No. 3,655,728 and can be prepared by reaction of the hydroxy and polyhydroxyaromatic acids with the alkylating agents of the formula:

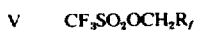

V    $CF_3SO_2OCH_2R_f$ in the presence of sodium bicarbonate, potassium bicarbonate or other metal bicarbonates in an inert solvent such as acetone. The resulting 1,1-dihydroperfluoroalkoxy-substituted aromatic ester can, in turn, be hydrolyzed to the free acid (compounds of Formula II wherein Z is OH).

The compounds of Formulae III and IIIA are generally known to the art, or can be conveniently prepared by methods known in the art. Thus, compounds III can be prepared from the corresponding compounds IIIA by catalytic reduction. In addition, certain compounds of types III and IIIA can be prepared by reduction of the corresponding oximes which are themselves prepared from the corresponding aldehydes by reaction with hydroxyamine hydrochloride.

The following examples will more fully illustrate the preparation of the compositions of the invention. All temperatures in the examples are given in degrees Centigrade. Examples 1–13 relate to the preparation of intermediate compounds and the remaining examples relate to the preparation of compounds of the invention.

EXAMPLE 1

A soluton of 2-aminomethylpyridine (0.20 mole, 21.6 g.) in glyme (200 ml) is treated dropwise over 40 minutes with 2,2,2-trifluoroethyl 2,5-bis(2,2,2-trifluoroethoxy)benzoate (0.10 mole, 40 g.) and the resulting mixture is stirred at about 25° C, for about 60 hours, heated and maintained at reflux temperature for about one hour. Next the mixture is evaporated to dryness, triturated with water and the resulting material is filtered. The solid is rinsed well with water, dried in an oven under vacuum then recrystallized from a 5 to 3 mixture of cyclohexane and carbon tetrachloride after treatment with decolorizing charcoal. The resulting product, after careful drying, is 2,5-bis(2,2,2-trifluoroethoxy)-N-(2-pyridylmethyl)-benzamide, a white solid, m.p. 102°–104° C.

This product is converted to a hydrochloride salt by dissolving 5.0 g. of the product in diethyl ether (150 ml.) with the addition of a small amount of ethyl acetate to effect solution. To this solution is added a saturated diethyl ether solution of hydrogen chloride gas until the pH of the mixture is acidic. The product precipitates and is separated by filtration. Recrystallization from a mixture of isopropanol and diethylether after treating with decolorizing charcoal provides a pure white hydrochloride salt, m.p. 190°–193° C.

| Analysis: | %C | %H | %N |
|---|---|---|---|
| Calculated for $C_{17}H_{14}F_6N_2O_3 \cdot HCl$: | 45.9 | 3.4 | 6.3 |
| Found: | 45.9 | 3.4 | 6.2 |

EXAMPLE 2

A solution of 3-aminopyridine (0.060 mole, 5.64 g.), triethylamine (0.12 mole, 12.1 g.) and glyme (100 ml.) is treated dropwise with a solution of 2,5-bis(2,2,2-trifluoroethoxy)benzoyl chloride (0.060 mole, 20.2 g.) and glyme (100 ml.). The combined solution is stirred and heated at its reflux temperature for about 40 hours then evaporated to remove the glyme and other volatile components. Excess 10% sodium hydroxide solution is added and the solution is further evaporated to remove triethylamine. The solid precipitate is separated by filtration, washed with water and dried carefully in an oven under vacuum. The resulting product, 2,5-bis(2,2,2-trifluoroethoxy)-N-(3-pyridyl)benzamide is treated with decolorizing charcoal then recrystallized from a mixture of isopropanol and carbon tetrachloride as fine white needles, m.p. 114°–117° C. Analysis of the product indicates that it crystallizes with ½ mole of carbon tetrachloride per mole of compound.

| Analysis: | %C | %H | %N |
|---|---|---|---|
| Calculated for: $C_{16}H_{12}F_6N_2O_3 \cdot ½ CCl_4$: | 42.2 | 2.6 | 6.0 |
| Found: | 42.1 | 2.6 | 6.0 |

Novel intermediates of the invention of Formula IV prepared from 2,5-bis(2,2,2-trifluoroethoxy)benzoic acid esters or acyl halides according to the methods of Examples 1 and 2 are given in Table I.

Table I

| Example Number | Compound | Melting Point (in °C.) |
|---|---|---|
| 3 | 2,5-bis(2,2,2-trifluoroethoxy)-N-(2-pyridyl)benzamide (isolated as the hydrochloride salt) | 166–179° |
| 4 | 2,5-bis(2,2,2-trifluoroethoxy)-N-(3-pyridylmethyl)-benzamide (isolated as the hydrochloride salt) | 181–188 |
| 5 | 2,5-bis(2,2,2-trifluoroethoxy)-N-(4-pyridyl)benzamide (isolated as the hydrochloride salt) | 164.5–166.5 |
| 6 | 2,5-bis(2,2,2-trifluoroethoxy)-N-[(6-methyl-2-pyridyl)methyl]benzamide | 113–114.5 |
| 7 | 2,5-bis(2,2,2-trifluoroethoxy)-N-[1-(2-pyridyl)-ethyl]benzamide | 98–100.5 |

Additional novel intermediates of Formula IV prepared according to the methods of Examples 1 and 2 are shown in Table II together with the intermediates utilized in their preparation.

Table II

| Example Number | Formula II | Formula III | Product of Formula IV |
|---|---|---|---|
| 8 | 3-OCH₂CF₃, 4-OCH₂CF₃-benzoyl chloride | 3-amino-1-methylpyrrole | 3,4-bis(2,2,2-trifluoroethoxy)-N-(1-methyl-3-pyrrolyl)benzamide |
| 9 | 2,4,6-tris(2,2,2-trifluoroethoxy)-phenyl 2,2,2-trifluoroethyl ketone | 2-(aminomethyl)pyridine | 2,4,6-tris(2,2,2-trifluoroethoxy)-N-(2-pyridylmethyl)benzamide |
| 10 | 2-(2,2,2-trifluoroethoxy)phenyl 2,2,2-trifluoroethyl ketone | 2-(aminomethyl)-4-methylpyridine | 2-(2,2,2-trifluoroethoxy)-N-[(4-methyl-2-pyridyl)methyl]benzamide |
| 11 | 2-(2,2,3,3,3-pentafluoropropoxy)phenyl 2,2,3,3,3-pentafluoropropyl ketone | 2-(aminomethyl)-6-methylpyridine | 2-(2,2,3,3,3-pentafluoropropoxy)-N-[(6-methyl-2-pyridyl)methyl]benzamide |
| 12 | 3,4-bis(2,2,2-trifluoroethoxy)phenyl 2,2,2-trifluoroethyl ketone | 2-(aminomethyl)pyridine | 3,4-bis(2,2,2-trifluoroethoxy)-N-(2-pyridylmethyl)benzamide |
| 13 | 2,6-bis(2,2,2-trifluoroethoxy)phenyl 2,2,2-trifluoroethyl ketone | 2-(aminomethyl)pyridine | 2,6-bis(2,2,2-trifluoroethoxy)-N-(2-pyridylmethyl)benzamide |

The following example illustrates the reduction of intermediates of Formula IV to provide compounds of the invention of Formula I.

EXAMPLE 14

2,5-Bis(2,2,2-trifluoroethoxy)-N-(3-pyridyl)benzamide (0.01 mole, 3.9 g.), 8.4 N hydrogen chloride in isopropanol (2.4 ml., 0.02 mole), platinum oxide (0.2 g.) and acetic acid (100 ml.) are shaken together on a Parr hydrogenation apparatus at a temperature of about 25° C. for about 4 hours. The mixture is filtered to remove all solid residue and the filtrate is concentrated by evaporation under vacuum. The residue is recrystallized from a mixture of ethanol and isopropanol after treating with decolorizing charcoal. The product is white needles of 2,5-bis(2,2,2-trifluoroethoxy)-N-(3-piperidyl)benzamide hydrochloride, m.p. 224°–225° C.

| Analysis: | %C | %H | %N |
|---|---|---|---|
| Calculated for $C_{16}H_{18}F_6N_2O_3$ HCl: | 43.9 | 4.4 | 6.4 |
| Found: | 43.7 | 4.5 | 6.3 |

The compounds of Examples 15–20 (which are shown in Table III) are prepared according to the method generally described in Example 14.

Table III

| Example Number | Product | Melting Point (in °C.) |
|---|---|---|
| 15 | 2,5-bis(2,2,2-trifluoroethoxy)-N-(2-piperidylmethyl)-benzamide hydrochloride | 228–229 |
| 16 | 2,5-bis(2,2,2-trifluoroethoxy)-N-(2-piperidyl)-benzamide hydrochloride, 3/4 hydrate | Glass, analysis acceptable |

Table III-continued

| Example Number | Product | Melting Point (in °C.) |
|---|---|---|
| 17 | 2,5-bis(2,2,2-trifluoro-ethoxy)-N-(3-piperidylmethyl)-benzamide hydrochloride | 189–191.5 |
| 18 | 2,5-bis(2,2,2-trifluoro-ethoxy)-N-(4-piperidyl)-benzamide hydrochloride | 193.5–195 |
| 19 | 2,5-bis(2,2,2-trifluoro-ethoxy)-N-[(6-methyl-2-piperidyl)methyl]benzamide hydrochloride | 215–222 |
| 20 | 2,5-bis(2,2,2-trifluoro-ethoxy)-N-[1-(2-piperidyl)-ethyl]benzamide | 95–97.5 |

EXAMPLE 21

Under a nitrogen atmosphere 2,2,2-trifluoroethyl 2,5-bis(2,2,2-trifluoroethoxy)benzoate (0.025 mole, 10.0 g.) is treated with small portions of 4-aminomethylpiperidine (0.25 mole, 28.5 g.) over a period of 15 minutes. The mixture is allowed to stir for about 2 hours, during which time it thickens. Glyme (25 ml.) is added and stirring is continued for about 16 hours at about 25° C. The resulting solution is evaporated to remove the solvent and 400 ml. of water is added. The product is separated by filtration, washed with water and dried under vacuum in an oven. This crude product, 2,5-bis-(2,2,2-trifluoroethoxy)-N-(4-piperidylmethyl)benzamide, has a melting point of 96°–99° C. It is dissolved in 100 ml. of ethyl acetate then 5.0 ml. of an 8.4 N solution by hydrogen chloride in isopropanol is added and the mixture is cooled at about 0° C. A product is separated and recrystallized from a mixture of ethyl acetate and isopropanol after treatment with decolorizing charcoal. This product is white crystals of 2,5-bis(2,2,2-trifluoroethoxy)-N-(4-piperidylmethyl)-benzamide hydrochloride, m.p. 179°–180° C.

| Analysis: | %C | %H | %N |
|---|---|---|---|
| Calculated for $C_{17}H_{20}F_6N_2O_3$ HCl: | 45.3 | 4.7 | 6.2 |
| Found: | 45.7 | 4.6 | 6.2 |

EXAMPLE 22

Under a nitrogen atmosphere 2-aminomethylpiperidine (0.249 mole, 28.4 g.) is treated dropwise over 25 minutes with 2,2,2-trifluoroethyl 2,5-bis(2,2,2-trifluoroethoxy)benzoate (0.0249 mole, 10.0 g.). After 3 hours 50 ml. of benzene is added to the thick mixture and stirred for about 40 hours at 45° C. The mixture is then concentrated under vacuum with heating to remove the volatile components. The residue solidifies after cooling, is steam distilled for further purification and is separated by filtration and extracted into dichloromethane. The dichloromethane solution is washed with saturated sodium chloride solution, and the organic layer is dried over anhydrous magnesium sulfate. The magnesium sulfate is removed by filtration and 4 ml. of 8.4 N hydrogen chloride is isopropanol is added to the dichloromethane solution with stirring. After two hours the mixture is cooled to about 0° C. and the crude product is collected by filtration, washed with diethyl ether and dried in a vacuum oven. After treatment with decolorizing charcoal and recrystallization from an equivolume mixture of isopropanol and methanol, the product, 2,5-bis(2,2,2-trifluoroethoxy)-N-(2-piperidylmethyl)benzamide hydrochloride, has a melting point of 228°–229° C.

| Analysis: | %C | %H | %N |
|---|---|---|---|
| Calculated for $C_{17}H_{20}F_6N_2O_3$ HCl: | 45.3 | 4.7 | 6.2 |
| Found: | 44.9 | 4.8 | 6.1 |

EXAMPLE 23

Starting with 2,2,2-trifluoroethyl 2,5-bis(2,2,2-trifluoroethoxy)benzoate and 2-(1-aminoethyl)piperidine and using the procedure illustrated in Examples 21 and 22, the product 2,5-bis(2,2,2-trifluoroethoxy)-N-[1-(2-piperidyl)ethyl]-benzamide, m.p. 95°–97° C., is obtained as white needles.

| Analysis: | %C | %H | %N |
|---|---|---|---|
| Calculated for $C_{18}H_{22}F_6N_2O_3$: | 50.5 | 5.2 | 6.5 |
| Found: | 50.6 | 5.3 | 6.5 |

EXAMPLE 24

Formaldehyde (0.048 mole, 1.44 g. of 38%), formic acid (0.12 mole, 5.5 g. of 85%) and 2,5-bis(2,2,2-trifluoroethoxy)-N-(2-piperidylmethyl)benzamide (0.020 mole, 8.3 g.) are stirred together and heated at reflux for about 12 hours. The mixture is then cooled to ambient temperature, 2.7 ml. of concentrated hydrochloric acid is added and it is reheated and maintained at reflux for about 5 hours. Next, the mixture is cooled to ambient temperature, made basic with 10% sodium hydroxide solution and diluted with water. The organic layer is extracted into dichloromethane and the dichloromethane solution is washed first with water then with a saturated sodium chloride solution and finally dried over anhydrous magnesium sulfate. The magnesium sulfate is removed by filtration and the filtrate is concentrated under vacuum to provide a solid residue which is recrystallized from cyclohexane after treatment by decolorizing charcoal. The product 2,5-bis(2,2,2-trifluoroethoxy)-N-[(1-methyl-2-piperidyl)-methyl]benzamide is a white solid m.p. 99°–102° C.

| Analysis: | %C | %H | %N |
|---|---|---|---|
| Calculated for $C_{18}H_{22}F_6N_2O_3$: | 50.5 | 5.2 | 6.5 |
| Found: | 50.5 | 5.3 | 6.5 |

EXAMPLE 25

A solution of 1-ethyl-2-aminomethylpiperidine (0.113 mole, 16.0 g.) and 50 ml. of glyme is treated dropwise over one hour with a solution of 22.5 g. (0.0565 mole) 2,2,2-trifluoroethyl 2,5-bis(2,2,2-trifluoroethoxy)benzoate and 50 ml. of glyme. The mixture is stirred for about 40 hours and the volatile components are removed by evaporation under vacuum with heating. The residue is steam distilled to remove excess base and extracted with dichloromethane. The resulting dichloromethane solution is washed with water, then with saturated sodium chloride solution, and dried over anhydrous magnesium sulfate. The magnesium sulfate is removed by filtration and the solvent by evaporation under vacuum. The residue is recrystallized from a mixture of cyclohexane and benzene after treatment by decolorizing charcoal. The product is ivory needles of 2,5-bis(2,2,2-trifluoroethoxy)-N-[(1-ethyl-2-piperidyl)-methyl]benzamide, m.p. 95°–97° C.

| Analysis: | %C | %H | %N |
|---|---|---|---|
| Calculated for $C_{19}H_{24}F_6N_2O_3$: | 51.7 | 5.5 | 6.3 |
| Found: | 51.9 | 5.6 | 6.2 |

EXAMPLE 26

Using the synthetic method illustrated in Example 23, 1-ethyl-2-aminomethyl pyrrolidine and 2,2,2-trifluoroethyl 2,5-bis(2,2,2-trifluoroethoxy)benzoate are reacted to provide a white solid, 2,5-bis(2,2,2-trifluoroethoxy)-N-[(1-ethyl-2-pyrrolidyl)methyl]benzamide, m.p. 78°–80° C.

| Analysis: | %C | %H | %N |
|---|---|---|---|
| Calculated for $C_{18}H_{22}F_6N_2O_3$: | 50.5 | 5.2 | 6.6 |
| Found: | 50.3 | 5.0 | 6.4 |

EXAMPLE 27

Isopropanol (10 ml.) is used to dissolve 2,5-bis-(2,2,2-trifluoroethoxy)-N-(2-piperidylmethyl)benzamide (0.005 mole, 2.07 g.) and one equivalent of acetic acid dissolved in 1 ml. of isopropanol is added. On cooling, a solid product is obtained and separated by filtration. The product is recrystallized from isopropanol to provide the desired acetate salt. M.p. 145°–147° C.

| Analysis: | %C | %H | %N |
|---|---|---|---|
| Calculated for $C_{17}H_{20}F_6N_2O_3 \cdot CH_3CO_2H$: | 48.1 | 5.1 | 5.9 |
| Found: | 47.9 | 5.2 | 5.8 |

A variety of pharmaceutically acceptable salts of the compound 2,5-bis(2,2,2-trifluoroethoxy)-N-(2-piperidylmethyl)-benzamide of the invention are made and described in Table IV. The synthetic procedure used is that described in Example 27.

Table IV

| Example Number | Acid | Solubility in Hot Water | Melting Point (in ° C.) |
|---|---|---|---|
| 28 | $H_2SO_4$ | > 2% | 100 |
| 29 | $H_3PO_4$ | > 5% | 210 |
| 30 | HOOC-CH=CH-COOH | > 5% | 122–124 |
| 31 | $CH_3SO_3H$ | > 10% | 115–121 |
| 32 | HCOOH | > 10% | 171–172 |
| 33 | 2-hydroxybenzoic acid (salicylic, OH/COOH on benzene) | insoluble | — |
| 34 | $CH_3(CH_2)_{14}COOH$ | insoluble | — |
| 35 | $CH_3CH_2COOH$ | > 10% | — |
| 36 | $CH_2CH_2COOH$ / COOH | > 5% | — |

EXAMPLE 37

A mixture of 2.7 g. (0.0063 mole) of finely divided 2,5-bis(2,2,2-trifluoroethoxy)-N-[(1-methyl-2-piperidyl)methyl]-benzamide and 6 ml. of methyl iodide is heated at 56° to 57° C. in a sealed tube for about 90 minutes. The mixture is extracted with methanol, and the methanol extracts are concentrated to provide a crystalline solid which is recrystallized from 50 ml. of ethyl acetate and about 2 ml. of isopropanol, with treatment by decolorizing charcoal. The resulting product is dried to provide white solid 2-[2,5-bis(2,2,2-trifluoroethoxy)benzamidomethyl]-1,1-dimethylpiperidinium iodide, m.p. 170°–172.5° C.

| Analysis: | %C | %H | %N |
|---|---|---|---|
| Calculated for $C_{19}H_{25}F_6IN_2O_3$: | 40.0 | 4.4 | 4.9 |
| Found: | 40.3 | 4.4 | 5.1 |

EXAMPLE 38

Using the method of Example 37, 2,5-bis(2,2,2-trifluoroethoxy)-N-[(1-ethyl-2-piperidyl)methyl]benzamide is reacted with methyl iodide to provide 2-[2,5-bis(2,2,2-trifluoroethoxy)benzamidomethyl]-1-ethyl-1-methylpiperidinium iodide as a white solid, m.p. 162°–165° C.

| Analysis: | %C | %H | %N |
|---|---|---|---|
| Calculated for $C_{20}H_{27}F_6IN_2O_3$: | 41.1 | 4.7 | 4.8 |
| Found: | 40.8 | 4.7 | 4.8 |

Additional compounds of the invention, prepared using the method described in earlier examples, are shown in the following table:

Table V

| Example No. | Starting Materials | Method of Example No. | Product |
|---|---|---|---|
| 39 | 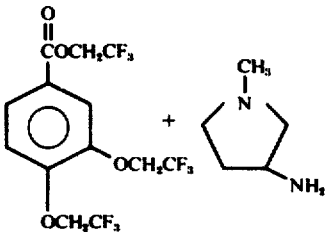 | 23 | 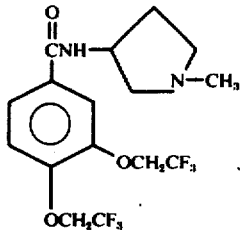 |
| 40 | 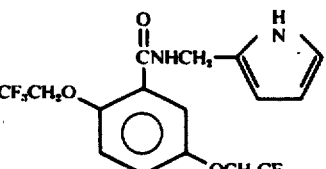 | 14 | 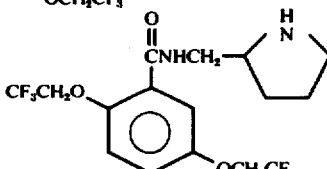 |
| 41 | 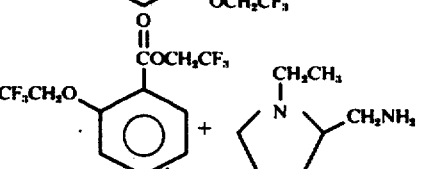 | 23 | 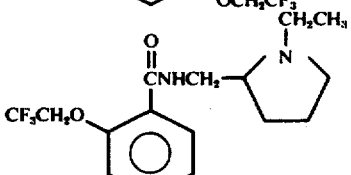 |
| 42 | 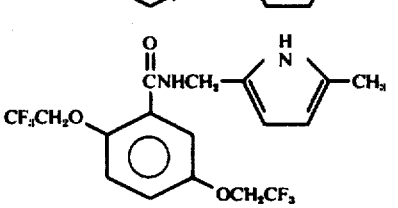 | 14 | 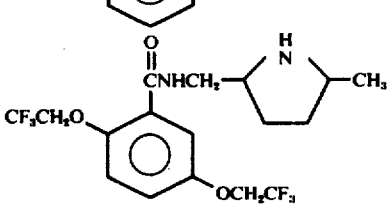 |

What is claimed is:

1. A compound of the formula

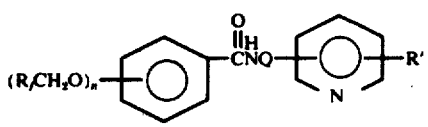

wherein $R_f$ is a perfluoroalkyl radical containing from one to three carbon atoms, $n$ is one to three, Q is a carbon-nitrogen bond, methylene or methylmethylene and R' is hydrogen, methyl or ethyl.

2. The compound 2,5-bis(2,2,2-trifluoroethoxy)-N-(3-pyridyl)benzamide according to claim 1.

3. The compound 2,5-bis(2,2,2-trifluoroethoxy)-N-[1-(2-pyridyl)ethyl]benzamide according to claim 1.

4. 2,5-Bis(2,2,2-trifluoroethoxy)-N-[(6-methyl-2-pyridyl)methyl]benzamide according to claim 1.

5. The compound 2,5-bis(2,2,2-trifluoroethoxy-N-(2-pyridylmethyl)benzamide according to claim 1.

6. The compound 2,5-bis(2,2,2-trifluoroethoxy)-N-(2-pyridyl)benzamide according to claim 1.

7. The compound 2,5-bis(2,2,2-trifluoroethoxy)-N-(3-pyridylmethyl)benzamide according to claim 1.

8. The compound 2,5-bis(2,2,2-trifluoroethoxy)-N-(4-pyridyl)benzamide according to claim 1.